United States Patent
Bratzler et al.

(10) Patent No.: US 10,363,258 B2
(45) Date of Patent: *Jul. 30, 2019

(54) TREATMENT OF MIGRAINES

(71) Applicant: Manistee Partners LLC, Concord, MA (US)

(72) Inventors: Robert L. Bratzler, Concord, MA (US); Martin Wand, Farmington, CT (US); Frederick Ryckman, West Chester, OH (US); Bradford J. Shingleton, Boston, MA (US)

(73) Assignee: Manistee Partners LLC, Concord, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/861,065

(22) Filed: Jan. 3, 2018

(65) Prior Publication Data

US 2018/0193354 A1 Jul. 12, 2018
US 2019/0022105 A9 Jan. 24, 2019

Related U.S. Application Data

(63) Continuation of application No. 15/110,295, filed as application No. PCT/US2015/010771 on Jan. 9, 2015, now Pat. No. 9,913,849.

(60) Provisional application No. 61/925,676, filed on Jan. 10, 2014.

(51) Int. Cl.
*A61K 31/5575* (2006.01)
*A61K 9/00* (2006.01)

(52) U.S. Cl.
CPC ........ *A61K 31/5575* (2013.01); *A61K 9/0014* (2013.01); *A61K 9/0048* (2013.01)

(58) Field of Classification Search
CPC . A61K 31/5575; A61K 9/0014; A61K 9/0048
See application file for complete search history.

(56) References Cited

U.S. PATENT DOCUMENTS

| | | | |
|---|---|---|---|
| 4,511,563 A | 4/1985 | Schmolka | |
| 4,767,619 A | 8/1988 | Murray | |
| 4,861,760 A | 8/1989 | Mazuel et al. | |
| 4,883,660 A | 11/1989 | Blackman et al. | |
| 5,264,206 A | 11/1993 | Bohn et al. | |
| 5,296,504 A | 3/1994 | Stjernschantz et al. | |
| 5,318,780 A | 6/1994 | Viegas et al. | |
| 5,346,692 A | 9/1994 | Wohlrab et al. | |
| 5,607,978 A | 3/1997 | Woodward et al. | |
| 5,665,773 A | 9/1997 | Klimko et al. | |
| 6,011,062 A | 1/2000 | Schneider et al. | |
| 6,224,887 B1 | 5/2001 | Samour et al. | |
| 6,689,901 B2 | 2/2004 | Henegar | |
| 6,927,300 B2 | 8/2005 | Gutman et al. | |
| 7,109,371 B2 | 9/2006 | Clissold et al. | |
| 7,157,590 B2 | 1/2007 | Gutman et al. | |
| 7,166,730 B2 | 1/2007 | Gutman et al. | |
| 7,351,404 B2 | 4/2008 | Woodward et al. | |
| 7,388,029 B2 | 6/2008 | Delong et al. | |
| 7,629,345 B2 | 12/2009 | Ongini et al. | |
| 7,674,921 B2 | 3/2010 | Maxey et al. | |
| 7,947,740 B2 | 5/2011 | Gutman et al. | |
| 8,227,514 B2 | 7/2012 | Rethore et al. | |
| 8,263,054 B2 | 9/2012 | Woodward et al. | |
| 9,913,849 B2 * | 3/2018 | Bratzler | A61K 31/5575 |
| 2003/0049307 A1 | 3/2003 | Gyurik | |
| 2003/0232070 A1 | 12/2003 | Samour | |
| 2007/0144540 A1 | 6/2007 | Henrich | |
| 2010/0010239 A1 | 1/2010 | Albert et al. | |
| 2010/0105771 A1 | 4/2010 | Delong et al. | |
| 2010/0234466 A1 | 9/2010 | Grosskreutz et al. | |
| 2010/0317595 A1 | 12/2010 | Mullins et al. | |
| 2011/0152264 A1 | 6/2011 | Reunamaki et al. | |
| 2012/0016136 A1 | 1/2012 | Biffi et al. | |
| 2012/0270946 A1 | 10/2012 | He et al. | |
| 2013/0150423 A1 | 6/2013 | Aung-Din et al. | |

FOREIGN PATENT DOCUMENTS

| | | |
|---|---|---|
| WO | WO 99/49835 A1 | 10/1999 |
| WO | WO 2009/103150 A1 | 8/2009 |
| WO | WO 2013/052380 A2 | 4/2013 |
| WO | WO 2013/052380 A3 | 4/2013 |

OTHER PUBLICATIONS

Extended European Search Report for EP 15 735 190.9, dated Nov. 2, 2017.
International Search Report and Written Opinion for PCT/US2015/010771 dated May 6, 2015.
International Preliminary Report on Patentability for PCT/US2015/010771 dated Jul. 21, 2016.
Third Party Observations submitted in connection with PCT/US2015/010771 submitted Apr. 8, 2016.
Antonova, Prostaglandins and prostaglandin receptor antagonism in migraine. Dan Med J. May 2013;60(5):B4635. Abstract Only.
Berge et al., Pharmaceutical salts. J Pharm Sci. Jan. 1977;66(1):1-19.
Gasser et al., Relation between blood flow velocities in the ophthalmic artery and in nailfold capillaries. Br J Ophthalmol. Apr. 1999; 83(4):505.
Hall et al., The effect of topical prostaglandins on migraine headaches. Association for Research in Vision and Ophthalmology (ARVO) Annual Meeting Poster Presentation, May 7-11, 2017. 1 page.
Hegyalijai et al., Cold-induced acral vasospasm in migraine as assessed by nailfold video-microscopy: prevalence and response to migraine prophylaxis. Angiology. Apr. 1997; 48(4):345-9.
Karagiannis et al., Cessation of migraines in a woman with low-tension glaucoma following the use of latanoprost: a favourable side effect? Eye (Lond). Feb. 2007;21(2):293-5. Epub Sep. 1, 2006.
Myren et al., Functional and molecular characterization of prostaglandin E2 dilatory receptors in the rat craniovascular system in relevance to migraine. Cephalalgia. Sep. 2010;30(9):1110-22. doi: 10.1177/0333102409357957. Epub Apr. 7, 2010.

(Continued)

*Primary Examiner* — Sudhakar Katakam
(74) *Attorney, Agent, or Firm* — Wolf, Greenfield & Sacks, P.C.

(57) ABSTRACT

Provided herein are prostaglandin $F_{2\alpha}$ analog compositions and methods for treating migraines.

23 Claims, No Drawings

(56) References Cited

OTHER PUBLICATIONS

Otto et al., Prostaglandins E1 and E2 interact with prostaglandin F2alpha to regulate initiation of DNA replication and cell division in swiss 3T3 cells. Proc Natl Acad Sci U S A. Aug. 1982;79(16):4992-6.
Weston, Migraine headache associated with latanoprost. Arch Ophthalmol. Feb. 2001;119(2):300-1.

* cited by examiner

TREATMENT OF MIGRAINES

CROSS-REFERENCE TO RELATED APPLICATIONS

This application is a continuation of and claims priority under 35 U.S.C. § 120 to U.S. Application, U.S. Ser. No. 15/110,295, filed Jul. 7, 2016, which is the National Stage of International Patent Application Serial No. PCT/US2015/010771, filed Jan. 9, 2015, which claims the benefit of the filing date of U.S. Provisional Application No. 61/925,676, filed Jan. 10, 2014, the entire contents of which are incorporated by reference herein.

BACKGROUND

Migraine is a type of headache, which is a severe, seriously debilitating and usually unilateral form of episodic headache that may be preceded by aura and that is frequently associated with both neurological and gastrointestinal symptoms such as nausea, vomiting, diarrhea, sensitivity to light (photophobia), sound (phonophobia), and smells (osmophobia); sleep disruption, and depression. When untreated, a migraine headache attack may last anywhere from four to 72 hours. Migraines include cluster headaches and vascular headaches and are sometimes termed sick headaches or histamine headaches.

Migraine can be divided into two major subtypes: migraine without aura and migraine with aura. Migraine without aura (MO) is a clinical syndrome characterized by headache attacks lasting 4-72 hours. Typical characteristics of the headache are unilateral location, pulsating quality (throbbing), moderate or severe intensity, aggravation by physical activity (which causes a mechanical strain on meningeal blood vessels) and association with nausea, vomiting, photophobia and/or phonophobia. About 70% of subjects suffering from migraines have migraine without aura. In migraine with aura (MA), attacks are accompanied by reversible focal neurological symptoms (mostly visual, but also sensory or motor symptoms). Aura develops over 5-20 minutes and lasts for less than 60 minutes. Headache with the features of MO usually follows the aura. About 30% of subjects suffering from migraines have migraine with aura.

Other, less common, types of migraine exist and include migraine with prolonged aura (aura symptoms last longer than 60 minutes); migraine aura without headache; migraine with acute onset aura; basilar migraine which can be associated with vertigo, gait perturbances and/or loss of consciousness; ophthalmoplegic migraine associated with ocular paralysis, diplopia and/or ptosis; retinal migraine; and familial hemiplegic migraine associated with hemiparesis or hemiplegia.

Pharmacological interventions for the management of migraine can be categorized into two general strategies: prevention of pain and/or associated symptomology and treatment to relieve/stop the pain and associated symptomology. It is commonly held that prostaglandin activity is associated with migraine and that blocking the activity of prostaglandins is an effective treatment for migraines.

SUMMARY OF THE INVENTION

It has been discovered, unexpectedly, that topical treatment with prostaglandins reduces the frequency, severity and duration of migraines. Without wishing to be bound by any particular theory of the invention, it is believed that migraines are successfully treated with prostaglandins due to the low systemic levels of prostaglandin resulting from topical treatment.

According to aspects of the invention, a method of treating migraine is provided. The method involves administering topically to a subject in need thereof a composition including a prostaglandin $F_{2\alpha}$ analog or pharmaceutically acceptable salt thereof, in an amount effective to treat migraine. The treatment may be administered prophylactically or therapeutically. Topical administration is to the epidermis, conjunctival surface or other mucous membranes, typically to a nail, the skin, the hair, the surface of the eye or the inner surface of the eyelid, and the like. It also may be application or delivery to mucosal surfaces, such as buccal, rectal and pulmonary tissue, including, for example, by sublingual, suppository or inhaled delivery. In any of the foregoing embodiments, the prostaglandin $F_{2\alpha}$ analog can be latanoprost, isopropyl unoprostone, bimatoprost, travoprost, or tafluprost; or pharmaceutically acceptable salt thereof. In some embodiments, the prostaglandin $F_{2\alpha}$ analog or pharmaceutically acceptable salt thereof is bimatoprost or a pharmaceutically-acceptable salt thereof.

It also is contemplated that the formulation be delivered other than topically, but in amounts that will achieve the doses appropriate for the practice of the invention. Such delivery includes oral and sustained release formats.

In any of the foregoing embodiments, the prostaglandin $F_{2\alpha}$ analog or pharmaceutically acceptable salt thereof may be administered in conjunction with a migraine drug that is not a prostaglandin $F_{2\alpha}$ analog or pharmaceutically acceptable salt thereof. The administration may be at the same time (in the same or different formation and mode of administration) or in a scheme involving administration at separate times and by the same or separate routes of administration. In one embodiment, the prostaglandin $F_{2\alpha}$ analog or pharmaceutically acceptable salt thereof is administered prophylactically and the other drug is administered acutely, i.e., abortively. According to one aspect of the invention, a topical pharmaceutical composition is provided comprising a prostaglandin $F_{2\alpha}$ analog or pharmaceutically acceptable salt thereof and a migraine drug that is not a prostaglandin $F_{2\alpha}$ analog. The migraine drug that is not a prostaglandin $F_{2\alpha}$ analog may be any of the migraine drugs listed below. According to another aspect of the invention, a kit is provided including a topical pharmaceutical composition comprising a prostaglandin $F_{2\alpha}$ analog or pharmaceutically acceptable salt thereof and a non-topical dosage form of a migraine drug that is not a prostaglandin $F_{2\alpha}$ analog, such as, for example, an oral dosage form. The migraine drug that is not a prostaglandin $F_{2\alpha}$ analog may be any of the migraine drugs listed below.

These and other aspects of the invention are described below in great detail.

DETAILED DESCRIPTION

The invention involves, in some aspects, topically administering to a subject in need thereof a composition including a prostaglandin $F_{2\alpha}$ analog or pharmaceutically acceptable salt thereof, in an amount effective to treat migraine. Subjects as used herein means human subjects. A subject in need thereof is a subject with a history of migraines or pre-migraine symptoms. A subject in need thereof also can be a subject suffering from a migraine.

Administering topically means administering to the epidermis such as to the skin, the hair, the nails, or to a mucous membrane such as the surface of the eye, the conjunctiva, the rectum, the nose, throat or lungs, or a buccal cavity.

Prostaglandin $F_{2\alpha}$ analogs, as used herein, means prostaglandin $F_{2\alpha}$ analogs and prostamide $F_{2\alpha}$ analogs. Prostaglandin $F_{2\alpha}$ analogs are ligands for and bind to the prostaglandin $F_{2\alpha}$ receptor and/or prostamide $F_{2\alpha}$ receptors. Prostaglandin $F_{2\alpha}$(PGF$_{2\alpha}$-Z)-7-((1R,2R,3R,5S)-3,5-dihydroxy-2-((S,E)-3-hydroxyoct-1-enyl)cyclopentyl)hept-5-enoic acid)) has the structure:

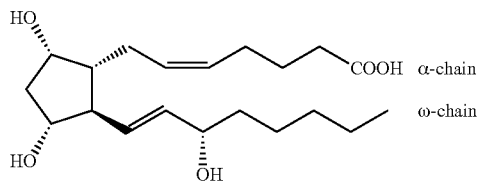

In some embodiments, a prostaglandin $F_{2\alpha}$ analog comprises two hydroxyl groups in cis configuration relative to the cyclopentane ring, and two side chains in a trans configuration relative to each other. The number of double bonds in the side chains and the substituents along the side chains as well as the length of the side chains may vary, depending on the analog. Examples of prostaglandin $F_{2\alpha}$ analogs include, but are not limited to, latanoprost, isopropyl unoprostone, bimatoprost, travoprost, and tafluprost. In some embodiments, the prostaglandin $F_{2\alpha}$ analog is bimatoprost. In some embodiments, the prostaglandin $F_{2\alpha}$ analog is bimatoprost, travoprost, or latanoprost. Several prostaglandin $F_{2\alpha}$ analogs are produced and available commercially, e. g., LUMIGAN® and LATISSE® (Allergan), XALATAN® (Pfizer), TRAVATAN® and TRAVATAN Z® (Alcon), TRAVO-Z™ (Micro Labs), RESCULA® (CIBA Vision), TAFLOTAN® (Santen Pharmaceutical Co.), and ZIOPTAN™ (Merck). Other forms of prostaglandin $F_{2\alpha}$ analogs are also contemplated, e.g., derivatives (including prodrugs) such as amides, lactones, ketones, acids, nitroderivatives, and esters of prostaglandin $F_{2\alpha}$ analogs (see, e.g. European Patent EP1501530 B1), as well as pharmaceutically acceptable salts of such analogs and derivatives. Examples of such other forms include, but are not limited to, 15-keto-latanoprost, 15-keto-bimatoprost, latanoprost nitroxide unoprostone, latanoprost free acid, travoprost free acid, fluprostenol free acid, tafluprost free acid, and bimatoprost free acid.

The above compounds and related prostaglandin $F_{2\alpha}$ analog compounds as well as synthesis thereof are well-known in the art and have been disclosed, e. g., in U.S. Pat. Nos. 5,296,504, 5,607,978, 5,665,773, 6,011,062, 6,689,901, 6,927,300, 7,166,730, 7,157,590, 7,109,371, 7,351,404, 7,388,029, 7,629,345, 7,674,921, 7,947,740, 8,227,514, 8,263,054 and U.S. Publication Nos. 2012/0270946, 2012/0016136A1, 2010/0105771, 2010/0010239, and 2011/0152264A1 (all of which are incorporated herein by reference).

A pharmaceutically acceptable salt is a salt that retains the desired biological activity of the parent compound and does not impart any unacceptable toxicological effects (see e.g., Berge, S. M., et al., 1977, J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous, and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids, and the like. Base addition salts include those derived from alkaline earth metals, such as sodium, potassium, magnesium, calcium, and the like, as well as from nontoxic organic amines, such as N,N'-dibenzylethylenediamine, Nmethylglucamine, chloroprocaine, choline, diethanolamine, ethylenediamine, procaine, and the like.

Migraine treatments are classified as prophylactic treatments or as therapeutic treatments. Each class of treatments is administered to the migraine sufferer based on the frequency and severity of the headache and its associated symptoms. For frequent migraines, prophylactic treatments are employed to reduce the frequency of migraines and also to reduce the severity and duration of migraines and their associated symptoms when they occur. For occasional migraines, therapeutic treatments are used to eliminate or reduce the severity and duration of the migraine and its associated symptoms after the migraine has begun.

Dosage regimens are adjusted to provide the optimum desired response. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms can be dictated by and directly dependent on (a) the unique characteristics of the active compound and the particular therapeutic effect to be achieved, and (b) the sensitivity in individuals to the active compound.

The pharmaceutical compositions disclosed herein may include a therapeutically effective amount of a prostaglandin $F_{2\alpha}$ analog disclosed herein. A "therapeutically effective amount" refers to an amount effective, at dosages and for periods of time necessary, to achieve the desired therapeutic result (e.g., to reduce the frequency of migraines and/or reduce the severity and duration of migraines and their associated symptoms). The effective amount of the active compounds may be determined by one of ordinary skill in the art but will vary depending on the compound employed, the frequency of application and the desired result. The effective amount of the composition may also vary according to factors such as the disease state, age, sex, and weight of the subject.

Typically, the dose to be administered will generally range from about 0.000001 to about 50% by weight of the composition, preferably from about 0.001 to about 50% by weight of the composition, and more preferably from about 0.1 to about 30% by weight of the composition. Dosage values may vary with the type and severity of the condition to be alleviated or treated. For a particular subject, specific dosage regimens can be adjusted over time according to the individual need and the professional judgment of the person administering or supervising the administration of the compositions.

According to certain aspects of the invention, the dosage form is a topical formulation containing a particular prostaglandin $F_{2\alpha}$ analog. Suitable compositions for topical administration include drops, solutions, powders, ointments, creams, lotions, pastes, gels, foams, viscous liquids, semisolids, lacquers/polishes (e.g., pigmented or non-pigmented nail polish or lacquer), suspensions, emulsions, microemulsions, reverse emulsions, colloids, dispersions, etc., which releases the prostaglandin $F_{2\alpha}$ analog or salt thereof, alone or together with one or more other drugs, at a predetermined rate over a defined period of time to a defined site of application. The system of administration may include an applicator system or a transdermal delivery system such as a drug-containing device (including e.g., patch, disc, etc.) which releases one or more drugs at a predetermined rate, the types of which are well known in the art. In some embodiments, topical administration involves applying a prostaglandin $F_{2\alpha}$ analog to the skin. The area of the skin may be an area normally experiencing hair growth or an area that does not normally experience hair growth, e.g. the dorsal tip of a phalanx (finger or toe) of a subject. In some embodiments, compositions of the invention are applied topically to at least one nail of the subject. In some embodiments, compositions of the invention are applied topically to at least two nails (e.g., two, three, four or five nails) of the subject. The compositions may be applied to the whole nail, or at least one part of the nail, e.g., the cuticle, nail matrix, or the tip or end of the nail plate. The compositions may also be applied to the skin surrounding to the nail. The prostaglandin $F_{2\alpha}$ analog also may be applied to an ocular surface or to another mucosal surface.

Topical formulations may be prepared directly, or by combining a prostaglandin $F_{2\alpha}$ analog-containing concentrate with a diluent, for example, an aqueous diluent. Such topical formulations may include additional excipients as necessary, for example, to modify consistency of the rate of absorption of the prostaglandin $F_{2\alpha}$ analog component. Specific examples of pharmaceutically acceptable excipients useful for topical administration include olive oil, arachis oil, castor oil, mineral oil, petroleum jelly, dimethyl sulphoxide, chremophor, Miglyol 182 (commercially available from Dynamit Nobel Kay-Fries Chemical Company, Mont Vale, N.J.), an alcohol (e.g. ethanol, n-propyl alcohol, or iso-propyl alcohol), liposomes or liposome-like products or a silicone fluid. Preferred excipients are dimethyl sulphoxide and olive oil. Mixtures of at least two of any suitable excipients may be used.

In some embodiments, compositions of the invention are formulated as a polish or lacquer, e.g., a nail polish, for administration to the nail or at least one part of the nail. Polishes and lacquers for drug delivery are known in the art (see, e. g., WO 9949835, U.S. Patent Publications US 2003049307, US 2003232070, U.S. Pat. Nos. 6,224,887, and 5,264,206, and 5,346,692, all of which are incorporated herein by reference). Such formulations include, e.g., one or more solvents and one or more film-forming polymers. Suitable solvents include, but are not limited to, hydrocarbons, halogenated hydrocarbons, alcohols, ethers, ketones and esters customary in cosmetics, especially acetic and esters of monohydric alcohols (ethyl acetate, n-butyl acetate etc.). In some embodiments, the solvents can be mixed with aromatic hydrocarbons such as toluene and/or alcohols such as ethanol or isopropanol and/or aliphatic sulfoxides and sulfones such as, for example, dimethyl sulfoxide or sulfolane. In some embodiments, the film-forming polymer is insoluble in water. Such film-forming polymers include, but are not limited to, polyvinyl acetate, partially hydrolyzed polyvinyl acetate, copolymers of vinyl acetate, acrylic acid, crotonic acid, monoalkyl maleates, ternary copolymers of vinyl acetate, crotonic acid and vinyl neodecanoate, ternary copolymers of vinyl acetate, crotonic acid and vinyl propionate, copolymers of methyl vinyl ether and monoalkyl maleates, copolymers of fatty acid vinyl esters and acrylic acid or methacrylic acid, copolymers of N-vinylpyrrolidone, methacrylic acid and alkyl methacrylates, copolymers of acrylic acid and methacrylic acid or alkyl acrylates or alkyl methacrylates, polyvinyl acetals, polyvinyl butyrals, alkyl-substituted poly-N-vinylpyrrolidones, and alkyl esters of copolymers of olefins and maleic anhydride. In some embodiments, the at least one film-forming polymer is mixed with cellulose nitrate. Polish or lacquer formulations can also contain additives common in cosmetics, such as plasticizers based on phthalates or camphor, colorants or pigments, perlescent agents, sedimentation retardants, sulfonamide resins, silicates, perfumes, wetting agents such as sodium dioctylsulfosuccinate, and lanolin derivatives. Optionally, such formulations can also include one or more agents that increase drug flux to the nail, e.g., ungual permeation enhancers, such as oxacyclohexadecan-2-one, and keratolytic agents). Exemplary polish formulations include (1) Eudragit® RL 100, glycerol triacetate, butyl acetate, ethyl acetate and ethanol and (2) ethyl acetate, isopropanol and butylmonoester of poly(methylvinyl ether/maleic acid). Lacquers and polishes can be applied using standard applicators known in the art (e.g. a nail brush).

In some embodiments, compositions of the invention are formulated for topical use as described in U.S. Patent Publication 2010/0317595, the entire disclosure of which is incorporated herein by reference. For example, the composition may be formulated as an emulsion, colloid, suspension, semi-solid, solution, dispersion, capsule, gel, lotion, cream and the like. In some embodiments, the composition is a water-in-oil emulsion, the emulsion including hydrophobic components such as a pharmaceutically acceptable oil. In some embodiments, the emulsion contains at least one oil and at least one surfactant. The hydrophobic component may be present in an effective amount, for example, in an amount of up to about 0.01%-90% w/v but preferably from about 0.01-10% by w/v, 0.05%-5% w/v, 0.05%-2% w/v or 1.0%-1.5% by w/v. Examples of useful pharmaceutically acceptable oils include vegetable oils, animal oils, mineral oils, synthetic oils and the like and mixtures thereof. In alternate embodiments, the hydrophobic component may comprise or consist of one or higher fatty acid glycerides. In some embodiments, the hydrophobic component comprises or consists of castor oil.

Surfactants may also be present in amounts of up to about 0.01-10% by w/v, 0.05%-5% w/v, 0.05%-2% w/v or 1.0%-1.5% by w/v. Surfactants may include alcohols including carboxylated and ethoxylated alcohols, amine oxides, block polymers, fatty acids including carboxylic fatty acids, ethoxylated alkyl phenols, ethoxylated fatty esters, glycerol esters, lanolin-based derivatives, lignin derivatives, methyl esters, mono- and tri-glycerides, polyethylene glycols, polymeric surfactants, propoxylated and ethoxylated fatty acids, alcohols, or alkyl phenols, protein based surfactants, sucrose and glucose esters and derivatives. In preferred embodiments, the surfactant is a polysorbate and in particular polysorbate 80 but other surfactants may be used.

Any known pharmaceutically acceptable surfactants may be used, including nonionic, anionic, cationic, and combinations thereof. Nonionic surfactants are preferred, and especially those surfactants having a hydrophile/lipophile balance (HLB) of 10 or more. Alternatively, certain combinations of high- and low-HLB surfactants may be utilized; preferably, such mixed surfactants are used in ratio such that the aggregate surfactant HLB (when weighted according to proportions used) remains in excess of 10.

Examples of specific surfactants which may be used include, without limitation, polyoxyethylene castor oil derivatives, such as polyoxyethylene glycerol triricinoleate polyoxyl 35 castor oil (CREMOPHOR® EL, available from BASF Corporation), and polyoxyl 40 hydrogenated castor oil (CREMOPHOR® RH40, available from BASF Corporation); mono-fatty acid esters of poloxyethylene (20) sorbitan, such as polyoxyethylene (20) sorbitan monooleate (TWEEN® 80), polyoxyethylene (20) sorbitan monostearate (TWEEN® 60), polyoxyethylene (20) sorbitan monopalmitate (TWEEN® 40), and polyoxyethylene (20) sorbitan monolaurate (TWEEN® 20) (all available from ICI Surfactants, Wilmington, Del.); polyoxyethylene glycol 200 monostearate (MYRJ® 52, available from Calgene Chemicals, Skokie, Ill.); polyglycerol esters with a HLB of 10 or greater, such as decablyceryl mono- and dioleate and the like; and mixtures thereof.

In some instances (as when the compositions are prepared as semi-solids), it may be advantageous to use at least one additional low-HLB surfactant along with one or more of the above high-HLB surfactant. Examples of low-HLB auxiliary surfactants which may be used include, but are not limited to, polyglycerol oleates (such as CAPROL® 10G40); lecithins; glyceryl monooleate or monolinoleate mixtures (such as MYVEROL® 18-99 or 18-92); propylene glycol laurate; and sorbitan oleates such as sorbitan monooleate (SPAN® 80), sorbitan trioleate (SPAN® 85), and sorbitan sesquioleate (SPAN® 20) (all available from ICI Surfactants, Wilmington, Del.). The surfactant phase may comprise about 10% to 90% by weight of the composition. Preferably the surfactant comprises about 20% to about 70% of the composition, and more preferably about 40% to about 60%, by weight.

It may be desirable for compositions of the invention to have high viscosity to prevent spreading of a composition from one area of the body to other areas of the body. Accordingly, formulations may include components that increase viscosity, e.g., by including thickening agents such as polymers or salts. Exemplary thickening agents include, but are not limited to, polyethylene glycol, carbomer, AMMONYX® polymers, AMPHOSOL® polymers, NINOL® polymers, COCOAMIDOPROPYLAMINE OXIDE, LAURAMIDOPROPYLAMINE/MYRISTAMIDOPROPYLAMOXIDE, BIO-SOFT® 9966 T ANIONIC/NONIONIC BLEND, BIO-TERGE® AS-40 CG-P SODIUM C14-16 OLEFIN SULFONATE, STEPANMILD® L3 LAURYL LACTYL LACTATE, STEPAN® 745 GC PEG/PPG-6/2 Glyceryl Cocoate, and STEPAN® SLL-FB Sodium Lauroyl Lactylate.

In some embodiments, compositions of the invention are formulated for topical administration to areas of skin such as arms, legs, torso, and face. Exemplary formulations for topical administration to areas of skin include a formulation comprising tegacid, spermaceti, methylparaben, propylene glycol, and polysorbate 80, a formulation comprising white petrolatum and wool fat, a formulation comprising light liquid petrolatum and wool fat, a formulation comprising N-methyl purrolidone and propylene glycol, and a formulation comprising alcohol, dichlorodifluoromethane, and dichlorotetrafluoroethane.

In some embodiments, compositions of the invention are formulated for topical use as described in U.S. Patent Publication 20130150423, the entire disclosure of which is incorporated herein by reference. In this publication, certain topical formulation are described, including at least one water-insoluble, pharmacologically approved, alkyl cellulose or hydroxyalkyl cellulose, and the like. Alkyl cellulose or hydroxyalkyl cellulose polymers for use in topical formulations are described to include ethyl cellulose, propyl cellulose, butyl cellulose, cellulose acetate, hydroxypropyl cellulose, hydroxybutyl cellulose, and ethylhydroxyethyl cellulose, alone or in combination. In addition, a plasticizer or a cross linking agent may be used to modify the polymer's characteristics. For example, esters such as dibutyl or diethyl phthalate, amides such as diethyldiphenyl urea, vegetable oils, fatty acids and alcohols such as acid oleic and myristyl may be used in combination with the cellulose derivative. In certain embodiments described, the topical formulation may further include hydrocarbons such as liquid paraffin, vaseline, solid paraffin, microcrystalline wax, etc.; higher aliphatic alcohols such as cetyl alcohol, hexadecyl, alcohol, stearyl alcohol, oleyl alcohol, etc.; esters of higher fatty acids with higher alcohols such as beeswax, etc.; esters of higher fatty acids with lower alcohols such as isopropyl myristate, isopropyl palmitate, etc.; vegetable oils, modified vegetable oils, hydrous lanolin and its derivative, squalene, squalane; higher fatty acids such as palmitic acid, stearic acid, etc. and the like. In certain embodiments described, the topical formulation may further include emulsifiers and dispersing agents which include, for example, anionic, cationic and nonionic surfactants. Nonionic surfactants are preferred because of their low levels of irritation to skin. Typical of nonionic surfactants are fatty acid monoglycerides such as glyceryl monostearate, etc.; sorbitan fatty acid esters such as sorbitan monolaurate, etc.; sucrose fatty acid esters; polyoxyethylene fatty acid esters such as polyoxyethylene stearate, etc.; and polyoxyethylene higher alcohol ethers such as polyoxyethylene cetyl ether, polyoxyethylene oleyl ether, etc. In certain embodiments described, the topical formulation may include a gelling agent such as methylcellulose, ethylcellulose, hydroxyethylcellulose, hydroxypropyl-cellulose, hydroxypropylmethylcellulose, carboxymethylcellulose, carbomer, and the like. In certain embodiments described, the topical formulation described is an aqueous based topical formulation. Some examples of patents disclosing pharmaceutical compositions which rely upon an aqueous gel composition as a vehicle for the application of a drug are U.S. Pat. Nos. 4,883,660; 4,767,619; 4,511,563; 4,861,760; and 5,318,780, the entire disclosures of which are herein incorporated by reference.

Formulations suitable for pulmonary administration may comprise dry particles. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Dry powder compositions may include a solid fine powder diluent such as sugar and are conveniently provided in a unit dose form. Formulations for pulmonary delivery may provide the active ingredient in the form of droplets of a solution and/or suspension. Such formulations can be prepared, packaged, and/or sold as aqueous and/or dilute solutions and/or suspensions, optionally sterile, comprising the active ingredient, and may conveniently be administered using any nebulization and/or atomization device. Such formulations may be delivered by the mouth or the nose.

Formulations can be for buccal administration. Such formulations may, for example, be in the form of tablets, and/or lozenges made using conventional methods, and may contain, for example, active ingredient together with an orally dissolvable and/or degradable composition. Alternately, formulations for buccal administration may comprise a powder and/or an aerosolized and/or atomized solution and/or suspension comprising the active ingredient.

Formulations for rectal delivery include, for example, suppositories, which typically are a combination of the active compound with a suppository base. Suitable suppository bases are, for example, natural or synthetic triglycerides, paraffin hydrocarbons, polyethylene glycols, or higher alkanols. In addition, it is also possible to use gelatin rectal capsules which consist of a combination of the active compounds with a base. Possible base materials include for example liquid triglycerides, polyethylene glycols, or paraffin hydrocarbons.

Oral formulations can be liquids or solids. Solid dosage forms include capsules, tablets, pills, powders, and granules. In such solid dosage forms, the active ingredient is mixed with at least one inert, pharmaceutically acceptable excipient or carrier and/or (a) fillers or extenders, (b) binders, (c) humectants, (d) disintegrating agents, (e) solution retarding agents such as paraffin, (f) absorption accelerators such as quaternary ammonium compounds, (g) wetting agents, (h), and (i) lubricants. In the case of capsules, tablets, and pills, the dosage form may include a buffering agent.

Solid compositions of a similar type can be employed as fillers in soft and hard-filled gelatin capsules. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner.

The topical formulation may further include one or more preservatives, stabilizers, or anti-oxidants.

Examples of preservatives that may be used in a formulation according to the present invention include, but are not limited to, bacteriostatic compounds and other preservatives suitable for topical administration including various alcohols, sorbic acid and salts and derivatives thereof, ethylenediamine, monothioglycerol, and thimerosal.

Examples of stabilizers that may be present in a formulation according to the present invention include pH buffers suitable for topical administration, complexing agents, chelating agents and the like.

Examples of anti-oxidants that may be used in a formulation according to the present invention include ascorbic acid and its derivatives, e.g., ascorbyl palmitate, as well as butylated hydroxyanisole, butylated hydroxytoluene, sodium bisulfite, sodium metabisulfite, and others.

Other adjuvants that may be included in the drug formulation include carriers, tackifiers, pigments, dyes, and other additives that do not adversely affect the mechanical or adhesive properties of the formulation.

The preferred dosage regimen will generally involve regular, such as one, two, three or more times a day, every other day, every three days, weekly, in each case for a period of treatment of at least one month, at least three months, at least six months, or at least one year. The dosage regimen can be determined by one of skill in the art and may vary according to factors such as the disease state, age, sex, and weight of the subject.

As mentioned, without wishing to be bound by any theory of the invention, it is believed that supplying very low plasma levels of the prostaglandin $F_{2\alpha}$ analog produce the desired result. The dosages and plasma levels can be the same as those found useful for the treatment of glaucoma with such analogs.

For example, tafluprost is a prostaglandin F2α analogue administered to treat glaucoma. The chemical name for tafluprost is 1 methylethyl (5Z)-7-{(1R, 2R, 3R, 5S)-2-[1E)-3,3-difluoro-4-phenoxy-1-butenyl}-3,5-dihydroxycyclopentyl]5-heptenoate. It is supplied as a solution at 0.0015% (15-μg/mL) (Zioptan™, Merck). The dose is an eye drop once daily in an affected eye, with 0.3-mL (4.5-μg) tafluprost in the evening. Following instillation of one drop of the 0.0015% solution once daily into each eye of healthy volunteers, the plasma concentrations of tafluprost acid peaked at a median time of 10 minutes on both Days 1 and 8. The mean plasma $C_{max}$ of tafluprost acid were 26 pg/mL and 27 pg/mL on Day 1, and Day 8, respectively. The mean plasma AUC estimates of tafluprost acid were 394 pg min/mL and 432 pg min/mL on Day 1 and 8, respectively.

Latanoprost is a prostaglandin F2a analogue administered to treat glaucoma. Its chemical name is isopropyl-(Z)7[(1R, 2R,3R,5S)3,5-dihydroxy-2-[(3R)-3-hydroxy-5-phenylpentyl]cyclopentyl]-5-heptenoate. Latanoprost ophthalmic solution is supplied as a sterile, isotonic, buffered aqueous solution containing 50 micrograms of latanoprost per ml. The recommended dosage is one drop (1.5 μg) in the eye(s) once daily in the evening. The distribution volume in humans is 0.16±0.02 L/kg. The acid of latanoprost can be measured in aqueous humor during the first 4 hours, and in plasma only during the first hour after local administration.

Bimatoprost 0.01% and 0.03% ophthalmic solution is a synthetic prostamide analog administered to treat glaucoma. Its chemical name is (Z)-7-[(1R,2R,3R,5S)-3,5Dihydroxy-2-[(1E,3S)-3-hydroxy-5-phenyl-1-pentenyl]cyclopentyl]-5-N-ethylheptenamide. One drop of bimatoprost ophthalmic solution 0.03% administered once daily to both eyes of 15 healthy subjects for two weeks, resulted in blood concentrations that peaked within 10 minutes after dosing and were below the lower limit of detection (0.025 ng/mL) in most subjects within 1.5 hours after dosing. Mean $C_{max}$ and AUC0-24 hr values were similar on days 7 and 14 at approximately 0.08 ng/mL and 0.09 ng hr/mL, respectively, indicating that steady state was reached during the first week of ocular dosing. Bimatoprost is moderately distributed into body tissues with a steady-state volume of distribution of 0.67 L/kg. In human blood, bimatoprost resides mainly in the plasma.

Travoprost is a prostaglandin $F_{1\alpha}$ analog administered to treat glaucoma. Its chemical name is [1R-[1α(Z),2β(1E, 3R*),3α,5α]]-7-[3,5-Dihydroxy-2-[3-hydroxy-4-[3-(trifluoromethyl) phenoxy]-1-butenyl]cyclopentyl]-5-heptenoic acid, 1-methylethylester. Following absorption into the eye, the free acid form of travoprost interacts with the endogenous FP prostanoid receptor to enhance aqueous humor outflow and lower intraocular pressure (IOP). Travoprost is supplied as a 0.004% ophthalmic solution. The recommended dosage is one drop in the eye(s) once daily in the evening. Plasma concentrations of the free acid administered daily as a single drop in both eyes are below 0.01 ng/ml (the quantitation limit of the assay) in two-thirds of the subjects. In those individuals with quantifiable plasma concentrations (N=38), the mean plasma $C_{max}$ was 0.018±0.007 ng/ml (ranged 0.01 to 0.052 ng/mL) and was reached within 30 minutes.

The foregoing preparations of tafluprost, latanoprost, bimatoprost and travoprost may be administered to the eye in the above described daily doses to prevent or therapeutically treat migraine, as demonstrated in the examples. The preparations may be applied to one eye or both eyes. These solutions also may be administered to other epithelial tissues to achieve the same effects. For example, a single daily drop of such solutions to the base of the finger nail and adjoining skin (e.g., on one, two, three, four or five fingers of one hand or both hands) and permitting the solution to dry yields effective concentrations for preventing and/or therapeutically treating migraine. In some embodiments of any one of the preparations, the preparation may be applied to the eye or the nail area daily for at least one month (e.g., for one month, two months, three months, four months, five months, six months, or longer).

In some embodiments, compositions of the invention may include more than one therapeutic agent, e.g., a prostaglandin $F_{2\alpha}$ analog and at least one additional therapeutic agent that is not a prostaglandin $F_{2\alpha}$ analog which treats migraine (therapeutically or prophylactically). In some embodiments, the composition comprises a prostaglandin $F_{2\alpha}$ analog or pharmaceutically acceptable salt thereof, or a derivative thereof, formulated together with a drug which (i) is not a prostaglandin $F_{2\alpha}$ analog or pharmaceutically acceptable salt thereof, or a derivative thereof, and (ii) that is a drug which treats migraine.

In some embodiments, methods of the invention may include the use of a prostaglandin $F_{2\alpha}$ analog and at least one additional therapy which treats migraine (therapeutically or prophylactically), such as a therapeutic agent (e.g., a drug which treats migraine), a laser therapy, surgery, a device and/or a behavioral therapy.

Drugs which are known to treat migraine include therapeutic (abortive) and prophylactic drugs. Abortive treatments include the triptans, which specifically target serotonin. Examples include Almotriptan (AXERT®), Eletriptan (RELPAX®), Frovatriptan (FROVA®), Naratriptan (AMERGE®, NARAMIG®), Rizatriptan (MAXALT®), Sumatriptan (ALSUMA®, DosePro®, IMITREX®, SUMAVEL®, TREXIMET®, ZECUITY®), and Zolmitriptan (ZOMIG®). Other abortive migraine drugs are acetaminophen-isometheptene-dichloralphenazone (MIDRIN®), Dihydroergotamine (D.H.E. 45 Injection, Migranal Nasal Spray), and Ergotamine tartrate (Cafergot). In addition, over-the-counter medications such as Advil® Migraine (containing ibuprofen), Excedrin® Migraine (containing aspirin, acetaminophen, caffeine), and Motrin® Migraine Pain (containing ibuprofen) are known. Diclofenac is another non-steroidal anti-inflammatory drug ("NSAID"), known chemically as [(2,6-dichloro-anilino)-2-phenyl]-2-acetic acid, known to treat migraine. The following drugs are mainly used for nausea related to migraine headaches in addition to migraine treatment: Metoclopramide (REGLAN®), Prochlorperazine (COMPAZINE®) and Promethazine (PHENERGAN®). Some drugs are used for headache pain but are not specific for migraines. These include analgesics, narcotics, and barbiturates. Since they can be habit forming, they have drawbacks relative to non-additive compounds. Drugs used to prevent migraine include medications to treat high blood pressure: beta-blockers (propranolol (INDERAL®), timolol), calcium channel blockers (verapamil (COVERA®)); Antidepressants: amitriptyline (ELAVIL®), nortriptyline (PAMELOR®); Antiseizure medications: gabapentin (NEURONTIN®), topiramate (TOPAMAX®), valproic acid (Depakote®); and Botulinum toxin (BOTOX®).

Other exemplary additional therapies which treat migraine (therapeutically or prophylactically), include relaxation training, thermal biofeedback, electromyography biofeedback, cognitive-behavioral therapy, arterial surgery, trigger site release surgery, patent foramen ovale closure surgery, spinal cord stimulation, biofeedback stimulator devices, neurostimulator devices (e.g., a transcutaneous electrical nerve stimulation device), vestibular rehabilitation exercise, occipital nerve stimulation, acupuncture, and infrared laser therapy.

In some embodiments, the subject is not affected by or does not exhibit symptoms of and one or more of, any combination of, or all of: glaucoma, ocular hypertension, blepharospasm, eyelash hypotrichosis, Meniere's disease, tinnitus, hearing loss or a hair-thinning or baldness condition (e.g., alopecia or male-pattern baldness). In some embodiments, the subject is not being treated to prevent sunburn. In some embodiments, the subject is not being treated to improve nail health. In some embodiments, the subject is not in need of or being treated for any one or any combination of a reduction of body fat or is not affected by or exhibit symptoms of one or more of: Cushing syndrome, pseudo-Cushing syndrome, drug-induced obesity, HIV-related lipodystrophy, hypothyroidism, pseudohypoparathyroidism, hypothalamic obesity, polycystic ovarian disease, depression, binge eating, Prader-Willi syndrome, Bardet-Biedl syndrome, Cohen syndrome, Down syndrome, Turner syndrome, growth hormone deficiency, growth hormone resistance, and/or leptin deficiency or resistance.

EXAMPLES

Example 1

A 53 year old male subject was treated with ocular administration of travoprost 0.0004% once per day as a single drop in both eyes in the evening. The subject reported that he had no migraines after being on therapy for 30 days.

Example 2

A 63 year old male in good health with a history of migraine headaches (1-3 per week) directly related to classic triggers (cheese, red wine, alcohol, monosodium glutamate, shrimp, mushrooms, and lack of sleep) daily administered 1 drop (approximately 0.05 ml) of the prostaglandin, LUMIGAN® (bimatoprost ophthalmic solution), topically to the cuticle region of four finger nails on one hand. After 1 month, the frequency of headaches decreased from the typical pattern of 1-3 per week to blocks of time extending 2-3 weeks without any headaches.

After three months of daily topical administration of LUMIGAN®, treatment was discontinued. In the two months post treatment the frequency of migraine headaches returned to the pre-treatment level (1-3 per week).

LUMIGAN® treatment was then restarted with daily topical administration to four finger nails for four months. A similar decrease in frequency in headaches was observed after 1 month as noted with first treatment above. Upon cessation of treatment, the frequency of headaches returned to baseline levels (1-3 per week) after one month.

LUMIGAN® treatment was initiated again on four finger nails for two months with a similar decrease in frequency of headaches within one month, as noted with LUMIGAN® use previously.

For the next three months the administration was tapered to three finger nails without any loss of the therapeutic effect.

The dose was tapered further to two finger nails for one month with no change in headache frequency again. Treatment was stopped.

Within one month of cessation of LUMIGAN® treatment, migraine headache occurrence returned to baseline frequency.

Treatment then was restarted two months later with topical administration to three finger nails. A decrease with headache frequency was observed within the first two weeks post reinitiating treatment.

After two months the dose was reduced to topical administration to two finger nails for three months without return to the baseline headache frequency.

After three months the dose was tapered to daily topical administration to one finger nail. The migraine headache frequency returned to the pre-treatment baseline level (1-3 per week) within two weeks of the dose reduction.

After one month with administration to one finger nail only, the dose was increased to daily administration to two finger nails. Headache frequency was reduced within two weeks.

Dosage was maintained at two finger nails daily for another two months with continued reduction in headache frequency.

Example 3

A 32 year old female, with a history of experiencing migraine headaches daily, started treatment by administering a single drop of LUMIGAN® to each of four finger nails on one hand. The drops were maintained on the nail beds for five minutes. Within a couple of weeks, she rarely had a headache, and when she had the occasional headache, it was mild in comparison to pretreatment.

After ceasing treatment, the daily headaches returned.

Example 4

A 58 year old female, with a history of migraine headaches for forty years, had been seen by multiple headache specialists and had avoided all food triggers without reduction in headache frequency or intensity. After about 45 days of once-daily administration of a single LUMIGAN® drop to each of four finger nails on one hand, her headache frequency and severity decreased.

After ceasing treatment, the frequency and severity of headaches returned to pretreatment levels.

Example 5

A 54 year old male with a fifteen year history of severe migraine headaches refractory to multiple therapies, started treatment with TRAVATAN Z® (travoprost ophthalmic solution) administered topically to one eye daily. One month later the migraine headaches had totally resolved.

Example 6

A 64 year old female with a history of migraine headaches (one per week) was started on daily topical administration of the prostaglandin, XALATAN® (latanoprost ophthalmic solution), to both eyes daily. After six months of treatment, the frequency of migraine headaches was reduced to one per 6 months and the severity was much milder.

Example 7

A 47 year old male with a history of weekly migraine headaches started applying one drop of LUMIGAN® to each of three finger nails on one hand. After two weeks, the frequency and severity of the migraine headaches decreased and was maintained for three months of treatment.

Without further elaboration, it is believed that one skilled in the art can, based on the above description, utilize the present invention to its fullest extent. The specific embodiments are, therefore, to be construed as merely illustrative, and not limitative of the remainder of the disclosure in any way whatsoever. All publications cited herein are incorporated by reference for the purposes or subject matter referenced herein.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of treating migraine in a subject in need thereof, the method comprising oral or mucosal membrane administration of a composition comprising latanoprost, isopropyl unoprostone, bimatoprost, travoprost, or tafluprost, or a pharmaceutically acceptable salt thereof, to the subject, in an amount effective to treat migraine; provided that the mucosal membrane is not an eye.

2. The method of claim 1, wherein the administration to the subject reduces the frequency of migraines in the subject.

3. The method of claim 1, wherein the administration to the subject is therapeutic.

4. The method of claim 1, wherein the administration to the subject is oral administration.

5. The method of claim 1, wherein the administration to the subject is administration to a mucous membrane.

6. The method of claim 5, wherein the mucous membrane is of the rectum, nose, throat, lungs, or buccal cavity.

7. The method of claim 5, wherein the administration is sublingual, suppository, or inhaled delivery.

8. The method of claim 1, wherein the composition comprises bimatoprost, travoprost, or latanoprost, or a pharmaceutically acceptable salt thereof.

9. The method of claim 1, wherein the composition comprises bimatoprost, or a pharmaceutically acceptable salt thereof.

10. A method of treating migraine in a subject in need thereof, the method comprising sustained release administration of a composition comprising latanoprost, isopropyl unoprostone, bimatoprost, travoprost, or tafluprost, or a pharmaceutically acceptable salt thereof, to the subject, in an amount effective to treat migraine.

11. The method of claim 10, wherein the administration to the subject reduces the frequency of migraines in the subject.

12. The method of claim 10, wherein the administration to the subject is therapeutic.

13. The method of claim 10, wherein the sustained release administration to the subject is oral administration.

14. The method of claim 10, wherein the sustained release administration to the subject is topical administration.

15. The method of claim 14, wherein the topical administration comprises delivery of the composition by a transdermal delivery system.

16. The method of claim 15, wherein the transdermal delivery system is a drug-containing device which releases one or more drugs at a predetermined rate.

17. The method of claim 10, wherein the composition comprises bimatoprost, travoprost, or latanoprost, or a pharmaceutically acceptable salt thereof.

18. The method of claim 10, wherein the composition comprises bimatoprost, or a pharmaceutically acceptable salt thereof.

19. A method of treating migraine in a subject in need thereof, the method comprising administering, to the eye of the subject, a composition comprising isopropyl unoprostone, bimatoprost, travoprost, or tafluprost, or a pharmaceutically acceptable salt thereof, in an amount effective to treat migraine.

20. The method of claim 19, wherein the administration to the subject is reduces the frequency of migraines in the subject.

21. The method of claim 19, wherein the administration to the subject is therapeutic.

22. The method of claim 19, wherein the composition comprises bimatoprost or travoprost, or a pharmaceutically acceptable salt thereof.

23. The method of claim 19, wherein the composition comprises bimatoprost, or a pharmaceutically acceptable salt thereof.

* * * * *

UNITED STATES PATENT AND TRADEMARK OFFICE
CERTIFICATE OF CORRECTION

PATENT NO. : 10,363,258 B2
APPLICATION NO. : 15/861065
DATED : July 30, 2019
INVENTOR(S) : Robert L. Bratzler et al.

Page 1 of 1

It is certified that error appears in the above-identified patent and that said Letters Patent is hereby corrected as shown below:

In the Claims

In Claim 20, at Column 14, Lines 63-65, the text: "The method of claim 19, wherein the administration to the subject is reduces the frequency of migraines in the subject." should be replaced with: -- The method of claim 19, wherein the administration to the subject reduces the frequency of migraines in the subject. --.

Signed and Sealed this
Fourth Day of February, 2020

Andrei Iancu
*Director of the United States Patent and Trademark Office*